United States Patent [19]
Briggs et al.

[11] Patent Number: 5,936,074
[45] Date of Patent: Aug. 10, 1999

[54] TEICOPLANIN DEACYLATION PROCESS AND PRODUCT

[75] Inventors: Barbara Shreve Briggs; Robin David Grey Cooper, both of Indianapolis; Adam Joseph Kreuzman, Greenwood; Milton Joseph Zmijewski, Jr., Carmel, all of Ind.

[73] Assignee: Eli Lilly and Company, Indianapolis, Ind.

[21] Appl. No.: 09/053,668

[22] Filed: Apr. 1, 1998

Related U.S. Application Data

[60] Provisional application No. 60/043,107, Apr. 17, 1997.

[51] Int. Cl.$^6$ .......................... C07H 17/08; A61K 31/70; A61K 38/12
[52] U.S. Cl. .......................... 536/7.1; 435/227; 435/228; 514/25; 514/33; 514/62; 530/317; 536/17.2; 536/17.4; 536/18.5
[58] Field of Search .................................. 435/227, 228; 514/25, 33, 62; 530/317; 536/7.1, 17.2, 17.4, 18.4, 18.5

[56] References Cited

FOREIGN PATENT DOCUMENTS

| | | | |
|---|---|---|---|
| 0 276 740 | 8/1988 | European Pat. Off. | C07K 9/00 |
| 0 327 548 | 8/1989 | European Pat. Off. | C07K 9/00 |
| 0 351 597 | 1/1990 | European Pat. Off. | C07K 9/00 |
| 0 351 684 A2 | 1/1990 | European Pat. Off. | |
| 0 351 685 A2 | 1/1990 | European Pat. Off. | |
| 0 352 538 A2 | 1/1990 | European Pat. Off. | |
| 0 370 283 A2 | 5/1990 | European Pat. Off. | |
| WO 88/02755 | 4/1988 | WIPO | C07K 9/00 |

OTHER PUBLICATIONS

Jütten and Greven. "Oligosaccharide Antibiotics" From *Polysaccharides In Medicinal Applications*, Ed. By Severian, 1996.
Dumitriu. Publ. By Marcel Dekker, Inc., pp. 373–379.
Malabarba et al. *J. Med. Chem.*, vol. 32(11):2451–2460, 1989.
Carelli, A., et al., *J. Indust. Microbiol.*, 15, 429–433 1995.
Malabarba, A., et al., *J. Antibiotics*, XLIII(9), 1107–1121, 1990.
5th European Congress on Biotechnology, Copenhagen, Jul. 1990.
Chung, S.K., et al., *J. Antibiotics*, XXXIX(5), 652–653, 1986.
Borghi, A., et al., *J. Antibiotics*, 49(6), 607–609, 1996.
Hermann, R., et al.,*J. Antibiotics*, 49(12), 1236–1248, 1996.
Chemical Abstract 90–024097/04, Jul. 1988.
Chemical Abstract 90–024025/04, Jul. 1988.
The Merck Index, Twelfth Edition (Merck & Co., Inc., Rahway, N.Y., 1996) entry 9269.
Malabarba, A., et al., *Medicinal Research Reviews*, 17(1), 69–137 (1997).
Chemical Abstracts 1998, Registry No. 117251–05–5.
*J. Med. Chem*, 1994, 37, #19, 2988–90.
*J. Med. Chem*, 1989, 32, #2, 310–314.

*Primary Examiner*—Howard C. Lee
*Attorney, Agent, or Firm*—Kathleen R. S. Page

[57] ABSTRACT

The present invention is directed to deacyl teicoplanin, and to a process for preparing deacyl teicoplanin by reacting teicoplanin with ECB deacylase. Deacyl teicoplanin can be alkylated to produce compounds useful for their antibacterial activity.

3 Claims, No Drawings

TEICOPLANIN DEACYLATION PROCESS AND PRODUCT

CROSS REFERENCE

This application claims priority of Provisional application Ser. No. 60/043,107, filed Apr. 17, 1997.

BRIEF SUMMARY OF THE INVENTION

The present invention is directed to a process for deacylating the glycopeptide teicoplanin. The invention is also directed to the resulting deacylated product, herein called "deacyl teicoplanin", in which the acyl of the N-acyl-β-D-glucosamine has been removed. Deacyl teicoplanin is useful as an intermediate, in that the freed amine can be reacted to obtain products useful for their antibacterial activity.

DETAILED DESCRIPTION OF THE INVENTION

Teicoplanin is a known glycopeptide, which is marketed in certain countries for the control of Gram-positive bacterial infections. Teicoplanin is actually a complex of five major components, which have the following formulae:

wherein R represents:

(Z)-4-decenoyl,
8-methylnonanoyl,
n-decanoyl,
8-methyldecanoyl, or
9-methyldecanoyl, See The Merck Index, Twelfth Edition (Merck & Co., Inc., Rahway, N.Y., 1989), entry 9269; the first R is incorrectly listed as 4-dec$\underline{a}$noyl. The Merck Index reference, and the references contained in it, are incorporated herein by reference. For confirmation of the correct 4-dec$\underline{e}$noyl composition, see *J. Antibiotics*, Vol. XVIII, No. 9, 1107–1121 (1990), also incorporated herein by reference.

Despite the prominence of teicoplanin, and the fact that numerous structural modifications have been made on it, it has not hitherto been possible to obtain deacyl teicoplanin. See *Medicinal Research Reviews*, Vol. 17, No. 1, 69–137, bridging pages 77–78 (1997).

It has now been discovered that teicoplanin can be deacylated to the valuable intermediate deacyl teicoplanin, with the following structural formula:

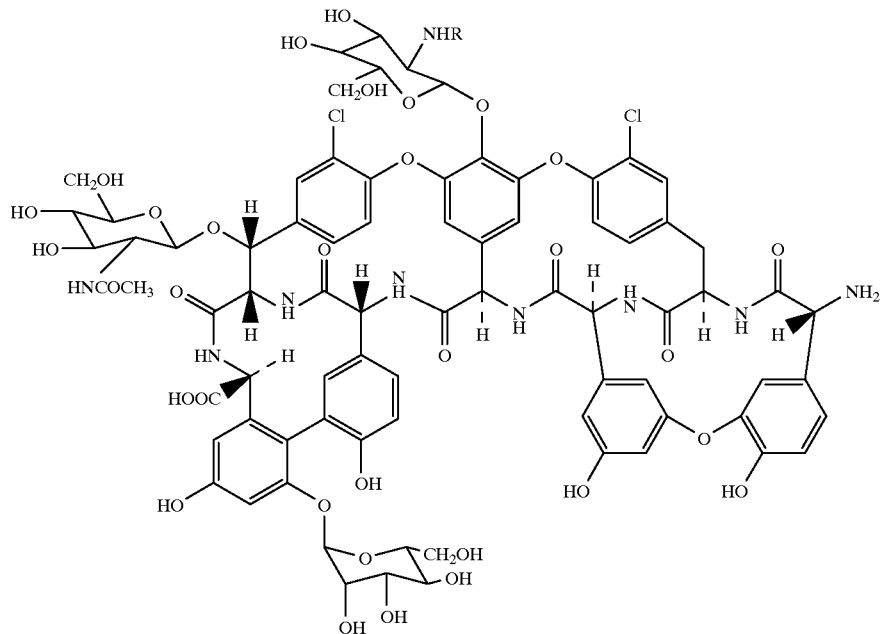

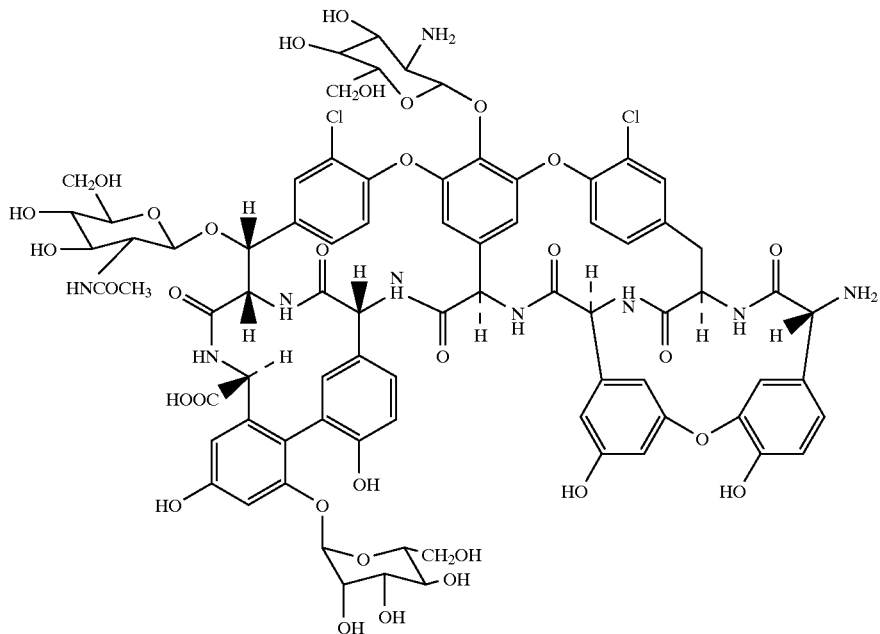

The teicoplanin is employed as the usual mixture, as a single factor, or as a mixture of any two or more factors.

The $N^{15}$ amine of the teicoplanin can be protected if desired. Amino protection and amino protecting groups are well known. See column 6 of U.S. Pat. No. 5,099,015, which is incorporated herein by reference. Special attention is directed to the references there cited, J. S. Barton, "Protective Groups in Organic Chemistry", J. G. W. McOmie, Ed., Plenum Press, New York, N.Y., 1973, Chapter 2; and T. W. Greene, "Protective Groups in Organic Synthesis," John Wiley and Sons, New York, N.Y., 1981, Chapter 7, which are also incorporated herein by reference.

Regardless of whether or not the $N^{15}$ amine is protected, the teicoplanin is reacted with a deacylating enzyme. Many such enzymes are known. However, applicants have discovered that one particular enzyme is unique in its ability to deacylate teicoplanin. This enzyme is known as echinocandin βdeacylase, or ECB deacylase, from its previously known ability to deacylate echinocandin β. ECB deacylase has also been used to deacylate A21978C and aculeacin. Consistent with prior nomenclature, this enzyme will be referred to herein as "ECB deacylase".

ECB deacylase is produced by certain microorganisms of the family Actinoplanaceae, preferably the microorganism *Actinoplanes utahensis* NRRL 12052. The preparation of ECB deacylase is taught in U.S. Pat. Nos. 4,293,482 and 4,304,716, at column 6 and column 4, respectively. These patents are incorporated herein by reference. The present deacylation of teicoplanin can be accomplished using whole cells or the crude or purified enzyme thereof, or using an immobilized form of the enzyme. See U.S. Pat. No. 5,573,936, which is directed to a process for purifying ECB deacylase, and which is incorporated herein by reference. ECB deacylase can also be produced by recombinant techniques; see *Appl. Microbiol. Biotechnol.* (1993) 39:532–536 and international patent application PCT/US95/08832.

The reaction of teicoplanin to produce deacyl teicoplanin (or an $N^{15}$-protected amino variation thereof) is carried out in accordance with usual enzymatic reactions. The teicoplanin and ECB deacylase enzyme are mixed in a liquid medium, typically water and preferably water adjusted to a pH of 5 to 8, preferably about 7 to 7.5. The deacylation proceeds at temperatures over a range of from 10 to 75° C.; conveniently, the reaction is conducted at temperatures of from 25 to 30° C. The deacylation is favored by mild agitation. Some deacylation occurs shortly after mixing the teicoplanin and ECB deacylase enzyme, but higher yields are obtained by maintaining the reaction mixture of the desired pH and temperature for a period of time, such as from 10 to 30 hours. Separation of the deacyl teicoplanin, and, if desired, purification, are carried out by conventional techniques. The deacyl teicoplanin can be converted to a salt, in conventional manners well known to those skilled in the art.

The following examples illustrate the present invention and will enable those skilled in the art to practice the invention.

EXAMPLE 1

Small Scale Synthesis of Deacyl Teicoplanin

A crude preparation of ECB deacylase determined to contain approximately 6000 mU/ml of deacylating activity was adjusted to pH 8.0 with 1N sodium hydroxide. Another aliquot of this enzyme preparation was adjusted to pH 7.23 and then filtered through a 0.45 μ filter to remove precipitate. Teicoplanin was added to 10 ml of each of these enzyme solutions for a final concentration of 1 mg of teicoplanin per ml. The remaining enzyme solutions were kept as controls. These reaction mixtures were incubated at 26° C. for about 24 hours on a shaker orbiting in a two-inch circle at 250 rpm. Methanol extracts of the reaction mixtures were examined on HPLC for the presence of bioconversion products. The chromatographs showed the disappearance of teicoplanin and the appearance of a new more polar peak. The HPLC system utilized was a gradient eluant system at 1.0 ml min$^{-1}$ on a Waters RCM 8×10 RadialPak containing a NovaPak C18 column cartridge with a μBondaPak C18 guard column with a detection at 280 nm. Gradient system was as follows: 0.2% aqueous trifluoroacetic acid/acetonitrile (95/5, v/v)

held for 3 minutes, ran 17 minute linear gradient to 0.2% aqueous trifluoroacetic acid/acetonitrile (60/40, v/v), then decreased to 0.2% aqueous trifluoroacetic acid/acetonitrile (95/5, v/v) in 5 minutes. Extract of pH 8.0 reaction was analyzed on LC/MS.

Mass spectral data were obtained using a Micromass Inc. (Beverly, Mass.) Quattro triple quadrupole mass spectrometer equipped with a pneumatically assisted electrospray (ESI) LC-MS interface. Data visualization and processing services were provided by the Masslynx software suite. The LC separation was performed using a Waters (Marlborough, Mass.) 610-MS pump controller and solvent delivery unit, a Waters 991 ultra-violet photodiode array (UV-PDA) detector controlled by an IBM-compatible 80386 computer running version 6.33a of the Waters Powerline control software package.

50 µL of each sample preparation was injected by a Waters WISP 712 autosampler and separated on the same column described above. The column effluent, after passing through the UV-PDA, was split by a Supelco Inc. (Bellefonte, Pa.) low dead-volume tee, one side of which (the waste line) was connected to a S.G.E. Inc. (Austin, Tex.) variable flow restrictor (model MCVT-1) that was adjusted so that the flow to the mass spectrometer was approximately 50 µL/minute. The mass spectrometer was calibrated for scanning from m/z 150 to m/z 2000 in 1.9 seconds using as a reference the ions produced when a solution of potassium iodide in a 50/50 mixture of isopropanol and deionized water was infused directly into the ESI interface at approximately 10 µL/minute. A gradient elution method was used: the weak starting eluent was a 5% aqueous solution of acetonitrile containing 0.2% (v/v) trifluoroacetic acid (TFA), and the strong eluent was a 40% acetonitrile solution containing 0.2% (v/v) TFA.

The data confirmed the presence of teicoplanin in the control and test sample; the doubly charged molecular ion of m/z940.8. The peak of interest eluting earlier than teicoplanin in the test sample gave a doubly charged molecular ion of mass 863.8. This is 77 m/z units less than the teicoplanin ion, or 154 amu since these were doubly charged ions. Hydrolysis of the fatty acid side chain would involve the net loss of $C_9H_{18}CO$ which corresponds to a change in mass of −154 amu. Thus, the LC/MC analysis confirmed that teicoplanin was deacylated to deacyl teicoplanin.

EXAMPLE 2

Preparative Scale Synthesis of Deacyl Teicoplanin

A crude preparation of ECB deacylase determined to contain approximately 15,000 mU of deacylating activity (1.3 liters) was adjusted to pH 7.5 with concentrated ammonium hydroxide. Teicoplanin (1 gram) was added to this enzyme solution maintaining pH at 7.5 with base. Temperature was maintained at 26° C. and pH was maintained at 7.5 by adding 1N ammonium hydroxide or iN hydrochloric acid. After 17 hours under these conditions, HPLC analysis of the reaction mixture indicated that approximately 70% of the teicoplanin was hydrolyzed. HPLC data indicated that additional reaction time under the conditions stated above did not improve yield. The hydrolysis of teicoplanin was monitored by HPLC utilizing a gradient eluent system at 1.0 ml min$^{-1}$ on a Waters RCM 8×10 RadialPak containing a NovaPak C18 column cartridge with a µBondaPak C18 guard column with a detection at 280 nm. Gradient system was as follows: 0.2% aqueous trifluoroacetic acid/acetonitrile (95/5, v/v) held for 3 minutes, ran 17 minute linear gradient to 0.2% aqueous trifluoroacetic acid/acetonitrile (60/40, v/v), then decreased to 0.2% aqueous trifluoroacetic acid/acetonitrile (95/5, v/v) in 5 minutes. A second 1 gram reaction was conducted as described above.

EXAMPLE 3

Purification of Deacyl Teicoplanin

The first of the bioconversion broths containing teicoplanin and its nucleus, from the preceding example, was loaded onto a 70 ml steel column (1.0"×18.0") of HP-20 SS resin set in $H_2O$. The column was washed with 800 ml of $H_2O$ and then eluted with a linear gradient of $H_2O$ to $CH_3CN$ over 90 minutes, at a flow rate of 25 ml/min. with a detection at 280 nm. The eluate was collected in twelve 200 ml fractions. These fractions were assayed by analytical HPLC. Analytical HPLC system used was a linear gradient system at 2 ml/min. on a Waters RCM 8×10 RadialPak containing a NovaPak C18 column cartridge with a detection from 200 to 550 nm. Gradient system was as follows: 0.2% aqueous trifluoroacetic acid/acetonitrile (95/5, v/v) to 0.2% aqueous trifluoroacetic acid/acetonitrile (50/50, v/v). Fractions identified to contain nucleus were pooled. The pool was concentrated to remove $CH_3CN$. This concentrate was loaded onto a 500 ml Rainin C18 preparative column (2.0"×17.0") set in 0.1% trifluoroacetic acid. The column was washed with 500 ml of 0.1% trifluoroacetic acid and then eluted with a linear gradient of 0.1% trifluoroacetic acid to 0.1% trifluoroacetic acid/$CH_3CN$ (3:1, v:v) over 60 minutes, at a flow rate of 40 ml/min. with a detection at 280 nm. Based on HPLC analysis, fractions containing the nucleus were pooled and then concentrated to a smaller volume. Dioxane was added to this concentrate before it was lyophilized. A yield of 0.731 g of bioconversion product (85% UV purity) was determined. Mass spectroscopy was conducted on this isolate utilizing a Finnigan TSQ 700 Instrument using Positive ESI by Direct Infusion. The Mass found=1726.7= M+H and 1748.6=M+Na.

The second of the bioconversion broths from the preceding example was worked up in the same manner except that pooling of the desired fractions was more selective during the purification work-up. As a result, a yield of 0.405 g of deacyl teicoplanin (92% UV purity) and 0.322 g of deacyl teicoplanin (85% UV purity) was obtained.

Approximately 13 mg of this last sample was dissolved in a mixture of $D_2O$ and $CD_3OD$ (1:2) and used to measure the NMR spectra. The spectra indicated predominantly a single compound and the absence of resonances due to the aliphatic side chain.

NMR spectra were measured on a Varian Unity Spectrometer using Nalorac Z.SPEC microsample Inverse Detection and PFG probes at 500 MHz ($^1$H) and 125 MHz ($^{13}$C). All NMR measure-ments were performed at 25° C. The sample was prepared by dissolving 20 mg of a previously $D_2O$-lyophilized sample in 0.25 ml of $D_2O$-$CD_3OD$ (2:1). $^1$H and $^{13}$C spectra were referenced with respect to solvent signals at 3.30 and 49 ppm, respectively. Carbon multiplicities were assigned by DEPT experiments. Standard pulse sequences were employed for COSY, TOCSY, ROESY, HMQC and HMBC experiments. Detailed analysis of $^1$H, $^{13}$C and 2D NMR (COSY, TOCSY, ROESY, HMQC and HMBC) data enabled assignment of protons and carbons of deacyl teicoplanin.

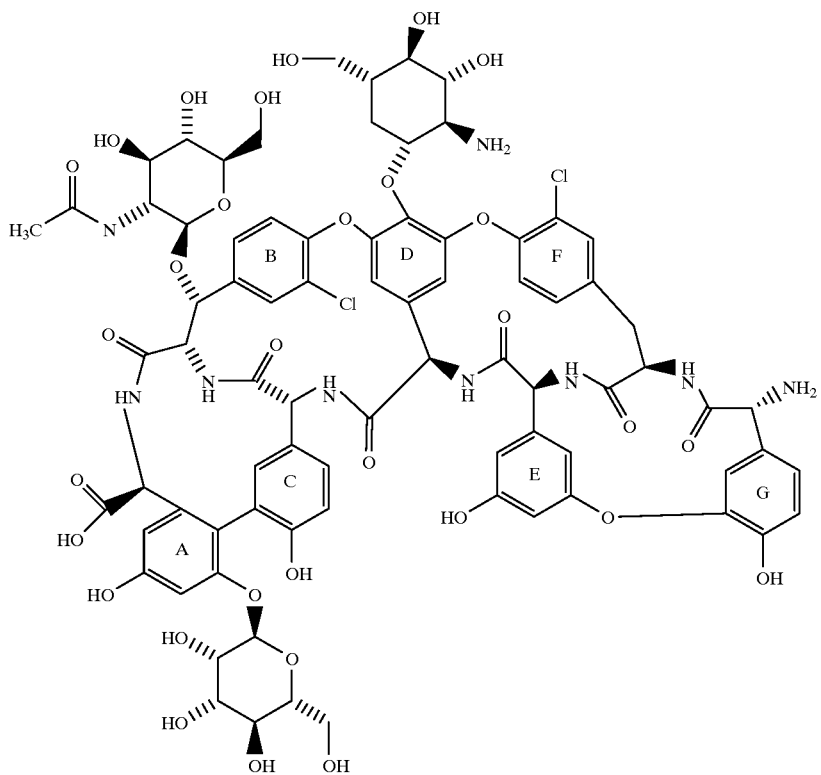
<u>$^1$H and $^{13}$C NMR Spectral Data of Deacyl Teicoplanin</u>
| Unit | Position | dH | Multiplicity (J in Hz) | dC |
|---|---|---|---|---|
| A | CO | | | 175.0 |
| | 1 | 4.81 | br | 57.8 |
| | 2 | | | 136.1 |
| | 3 | 6.54 | br | 109.2 |
| | 4 | | | 157.9 |
| | 5 | 6.87 | br | 103.3 |
| | 6 | | | 155.1 |
| | 7 | | | 121.4 |
| | 1' | 5.48 | obsc. | 97.7 |
| | 2' | 3.50$^a$ | m | 71.2$^c$ |
| | 3' | 3.65$^a$ | m | 74.1$^c$ |
| | 4' | 3.36$^a$ | m | 71.2$^c$ |
| | 5' | 3.49$^a$ | m | 77.7$^c$ |
| | 6'a | 3.89$^b$ | m | 61.7$^d$ |
| | 6'b | 3.73$^b$ | m | |
| B | CO | | | 169.6 |
| | 1 | 4.23 | br | 63.4 |
| | 2 | 5.50 | br | 79.4 |
| | 3 | | | 139.0 |
| | 4 | 7.72 | br | 129.6 |
| | 5 | | | 128.6 |
| | 6 | | | 150.5 |
| | 7 | 7.39 | d (8.5) | 124.9 |
| | 8 | 7.31 | brd (8.5) | 128.6 |
| | 1' | 4.56 | d (8.5) | 101.6 |
| | 2' | 3.72 | m | 56.8 |
| | 3' | 3.50$^a$ | m | 74.6$^c$ |
| | 4' | 3.42$^a$ | m | 70.7$^c$ |
| | 5' | 3.31$^a$ | m | 76.9$^c$ |
| | 6'a | 3.88$^b$ | m | 61.6$^d$ |
| | 6'b | 3.72$^b$ | m | |
| | CO | | | 175.3 |
| | CH3 | | s | 23.2 |
| C | CO | | | 169.5 |
| | 1 | 5.23 | s | 57.1 |
| | 2 | 6.80 | br | 144.4 |
| | 3 | | | 121.3 |
| | 4 | | | 124.1 |

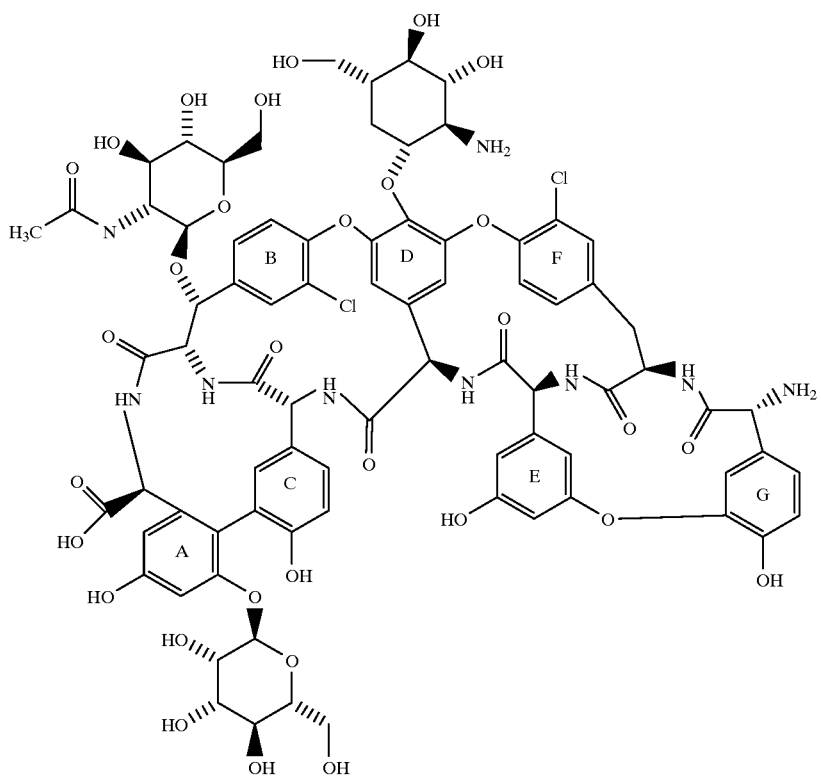
<u>$^1$H and $^{13}$C NMR Spectral Data of Deacyl Teicoplanin</u>
| Unit | Position | dH | Multiplicity (J in Hz) | dC |
|---|---|---|---|---|
| | 5 | 6.98 | d (8.5) | 149.9 |
| | 6 | 7.08 | brd (8) | 119.3 |
| | 7 | | | 128.6 |
| D | CO | | | 170.5 |
| | 1 | 5.59 | br | 55.9 |
| | 2 | | | 135.4 |
| | 3 | 5.21 | br | 105.5 |
| | 4 | | | 152.8 |
| | 5 | | | 132.8 |
| | 6 | 5.67 | br | 152.5 |
| | 7 | | | 108.4 |
| | 1' | 5.47 | obsc. | 101.5 |
| | 2' | 3.45 | m | 57.3 |
| | 3' | 3.71$^d$ | m | 70.2$^c$ |
| | 4' | 3.68$^a$ | m | 67.2$^c$ |
| | 5' | 3.44$^a$ | m | 73.1$^c$ |
| | 6'a,b | 6.84$^b$ | m | 61.1$^d$ |
| E | CO | | | 171.1 |
| | 1 | 5.55 | br | 59.5 |
| | 2 | | | 140.5 |
| | 3 | 6.49 | br | 110.8 |
| | 4 | | | 158.8 |
| | 5 | 6.63 | t (2) | 106.5 |
| | 6 | | | 160.7 |
| | 7 | 6.41 | br | 105.8 |
| F | CO | | | 172.3 |
| | 1 | 5.16 | m | 56.9 |
| | 2a | 3.37 | m | 37.6 |
| | 2b | 3.08 | brd (12.5) | |
| | 3 | | | 136.4 |
| | 4 | 7.29 | br | 132.1 |
| | 5 | | | 129.5 |
| | 6 | | | 151.0 |
| | 7 | 7.03 | d (8) | 125.0 |
| | 8 | 7.47 | brd (8) | 131.9 |
| G | CO | | | 172.0 |
| | 1 | 4.48 | obsc. | 55.0 |
| | 2 | | | 126.5 |

-continued

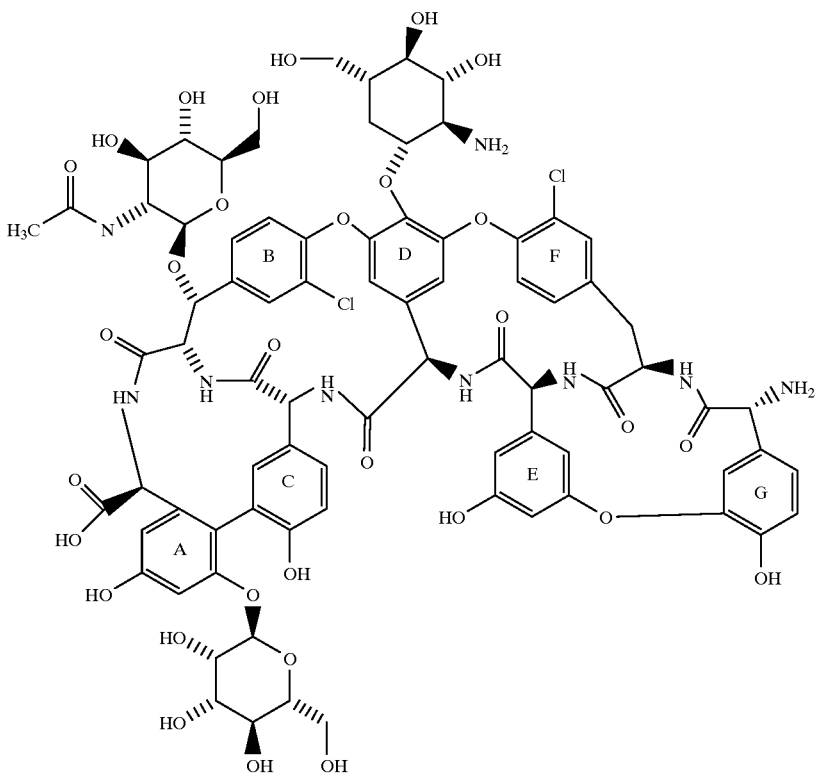

<u>$^1$H and $^{13}$C NMR Spectral Data of Deacyl Teicoplanin</u>

| Unit | Position | dH | Multiplicity (J in Hz) | dC |
|---|---|---|---|---|
| | 3 | 6.93 | br | 136.4 |
| | 4 | | | 122.1 |
| | 5 | | | 155.6 |
| | 6 | 6.86 | obsc. | 118.1 |
| | 7 | 6.94 | obsc. | 128.0 |

$^{a,b,c,d}$Assignments in each column may be interchanged.

EXAMPLE 4

Small Scale Synthesis of $N^{15}$ (tert-butoxycarbonyl) Deacyl Teicoplanin

A crude prepararation of ECB deacylase determined to contain approximately 15,000 mU/ml of deacylating activity and pH adjusted to 7.5 was added to the t-BOC derivative of teicoplanin. The reaction was conducted with 1 ml of enzyme preparation and 1 mg of substrate. Controls were run of the substrate in 100 mM phosphate buffer, pH 7.5 and of ECB deacylase. These reaction mixtures were stirred at ambient temperature for 17 hours. Methanol extracts of the reaction mixtures were examined on HPLC for the presence of bioconversion or degradation products. The chromatograph of the t-BOC teicoplanin bioconversion reaction showed the appearance of a new more polar peak which was not present in the controls. HPLC system utilized was a gradient eluant system at 1.0 ml min$^{-1}$ on a Waters RCM 8×10 RadialPak containing a NovaPak C18 column cartridge with a $\mu$BondaPak C18 guard column with a detection at 280 nm. Gradient system is as follows: 0.2% aqueous trifluoroacetic acid/acetonitrile (95/5, v/v) hold for 3 minutes, run 17 minute linear gradient to 0.2% aqueous trifluoroacetic acid/acetonitrile (60/40, v/v), then decrease to 0.2% aqueous trifluoroacetic acid/acetonitrile (95/5, v/v) in 5 minutes. The extract of the t-BOC teicoplanin bioconversion was analyzed on LC/MS, which verified the presence of the t-BOC deacyl teicoplanin.

Deacyl teicoplanin is useful in that its freed amine can be alkylated. The resulting alkylated products are useful for their antibacterial activity. The alkylation is accomplished by a reductive alkylation of deacyl teicoplanin. More particularly, deacyl teicoplanin is reacted with an aldehyde to form a Schiff's base, which is then reduced to the desired alkylated product. The reducing agent may be added simultaneously with the deacyl teicoplanin and the aldehyde. Whether carried out sequentially or simultaneously, the reaction is carried out in a polar solvent such as DMF, methanol, or a mixture of DMF and methanol, and at temperatures of from 25° to 100° C., preferably at temperatures of from 60° to 70° C., employing equimolar amounts or a slight excess of aidehyde. The reducing agent is also preferably employed in excess. A source of soluble copper may be added to the reaction mixture. Copper (II) acetate is a preferred source of copper. The copper is preferably supplied in an amount equimolar with the deacyl teicoplanin.

Reductive alkylation of deacyl teicoplanin yields compounds of the formula

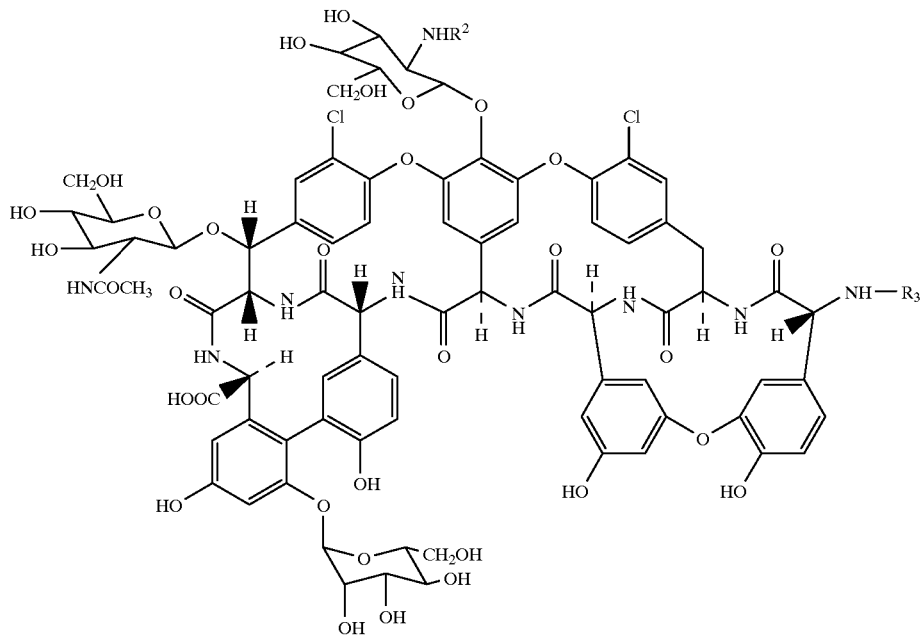

In the foregoing formula, one of $R^2$ and $R^3$ is: alkyl of $C_1$–$C_{12}$ wherein the attaching carbon is a $CH_2$, alkenyl of $C_2$–$C_{12}$ wherein the attaching carbon is a $CH_2$, alkynyl of $C_2$–$C_{12}$ wherein the attaching carbon is a $CH_2$, cycloalkylmethyl of the formula:

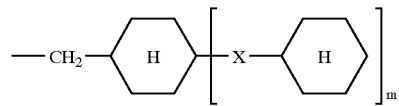

naphthylmethyl, thienylbenzyl, phenylthienylmethyl, benzyl of the formula:

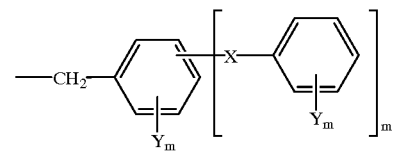

wherein X is a linker of the formula —$(CH_2)_x$—Z—$(CH_2)_y$—, wherein each of x and y is 0–6, and the sum of x and y=0–5, and Z is a bond, —O—, —S—, —CH=CH—, or —C≡C—;

and any Y is independently halo, loweralkyl of $C_1$–$C_5$, loweralkoxy of $C_1$–$C_5$, loweralkylthio of $C_1$–$C_5$, trifluoromethyl, or trifluoromethoxy, and each m is independently 0 or 1;

and the other of $R^2$ and $R^3$ is identical or is H, or, in the case of $R^3$, an amino protecting group.

These compounds, and their pharmaceutically acceptable salts, can be used to control and treat infections due to gram-positive bacteria, and especially gram-positive bacteria resistant to existing antibacterials, such as vancomycin-resistant enterococci ("VRE").

The alkylated compounds can be administered by any of the conventional techniques, including the oral route and parenteral routes such as intravenous and intramuscular. The amount of compound to be employed is not critical and will vary depending on the particular compound employed, the route of administration, the severity of the infection, the interval between dosings, and other factors known to those skilled in the art. In general, a dose of from about 0.5 to 100 mg/kg will be effective; and in many situations, lesser doses of from about 0.5 to 50 mg/kg will be effective. The compound can be administered in a single dose, but in the known manner of antibacterial therapy, the compound is typically administered repeatedly over a period of time, such as a matter of days or weeks, to ensure control of the bacterial infection.

Also in accordance with known antibacterial therapy, the alkylated product is typically formulated for convenient delivery of the requisite dose in a pharmaceutical formulation comprising one or more pharmaceutically-acceptable carriers. Such carriers are well known for both oral and parenteral routes of delivery. In general, a formulation will comprise a compound in a concentration of from about 0.1 to about 90% by weight, and often from about 1.0 to about 3%.

We claim:

1. A process for preparing a compound of formula (I)

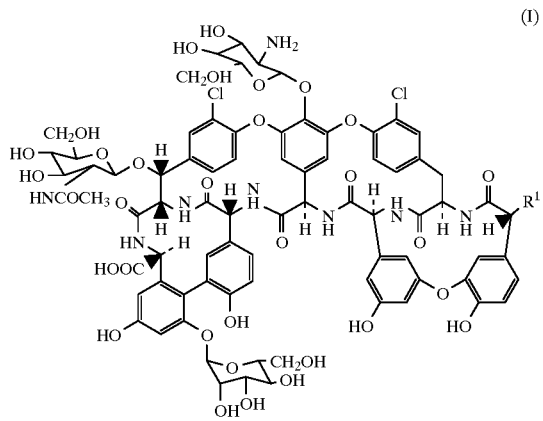

which comprises reacting a compound of the formula (II):

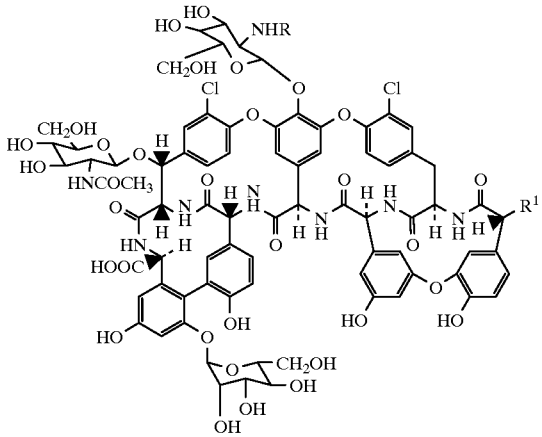

wherein R represents:
(Z)-4-decenoyl,
8-methylnonanoyl,
n-decanoyl,
8-methyldecanoyl, or
9-methyldecanoyl, and $R^1$ represents amino or protected amino, with ECB deacylase, and thereafter optionally forming a salt thereof, or removing the amino protecting group, or both forming a salt and removing the amino protecting group in either order.

2. A process of claim 1 wherein R is 8-methylnonanoyl.

3. A process of claim 1 which is conducted in water at a pH of from 7 to 7.5, and at a temperature of from 25 to 30° C.

* * * * *